(12) United States Patent
Borrello

(10) Patent No.: US 11,027,081 B2
(45) Date of Patent: Jun. 8, 2021

(54) METHOD AND SYSTEMS FOR PATIENT AIRWAY AND LEAK FLOW ESTIMATION FOR NON-INVASIVE VENTILATION

(71) Applicant: KONINKLIJKE PHILIPS N.V., Eindhoven (NL)

(72) Inventor: Michael Anthony Borrello, Carlsbad, CA (US)

(73) Assignee: Koninklijke Philips N.V., Eindhoven (NL)

(*) Notice: Subject to any disclaimer, the term of this patent is extended or adjusted under 35 U.S.C. 154(b) by 322 days.

(21) Appl. No.: 15/742,545

(22) PCT Filed: Jul. 6, 2016

(86) PCT No.: PCT/IB2016/054038
§ 371 (c)(1),
(2) Date: Jan. 8, 2018

(87) PCT Pub. No.: WO2017/006253
PCT Pub. Date: Jan. 12, 2017

(65) Prior Publication Data
US 2018/0200464 A1    Jul. 19, 2018

Related U.S. Application Data

(60) Provisional application No. 62/232,513, filed on Sep. 25, 2015, provisional application No. 62/189,522, filed on Jul. 7, 2015.

(51) Int. Cl.
*A61M 16/00*    (2006.01)
*A61M 11/00*    (2006.01)
(Continued)

(52) U.S. Cl.
CPC ......... *A61M 16/026* (2017.08); *A61M 11/00* (2013.01); *A61M 16/0003* (2014.02);
(Continued)

(58) Field of Classification Search
CPC .............. A61M 16/026; A61M 16/024; A61M 16/022; A61M 16/0605; A61M 16/0003;
(Continued)

(56) References Cited

U.S. PATENT DOCUMENTS 4,889,116 A * 12/1989 Taube ................... A61M 16/10
128/204.23
5,365,922 A * 11/1994 Raemer ................ A61B 5/0833
128/202.22
(Continued)

FOREIGN PATENT DOCUMENTS

EP    1270036 A2    1/2003
EP    2368593 A1    9/2011
(Continued)

OTHER PUBLICATIONS

Borrello:"Modeling and Control of Systems for Critical Care Ventilation"; 2005 American Control Conference, Jun. 2005, pp. 2166-2180.

*Primary Examiner* — Jan Christopher L Merene
*Assistant Examiner* — Brian T Khong
(74) *Attorney, Agent, or Firm* — Daniel H. Brean

(57) ABSTRACT

A method for estimating patient airway flow in a non-invasive ventilator system. The method includes the steps of (i) determining an estimated gas flow at the proximal end of the tubing; (ii) determining a proximal pressure error value by subtracting the measured pressure at the proximal end of the tubing from the estimated pressure at the proximal end of the tubing; (iii) compensating for the determined proximal pressure estimate error value; (iv) compensating for an error in the estimated gas flow at the proximal end of the tubing by feeding the estimate back into a sum of accumulated flows; (v) determining an estimated gas flow leak; (vi) monitoring for a leak in the non-invasive ventilator system;
(Continued)

(vii) determining a gas flow leak factor; (viii) adjusting the estimated gas flow leak; and (ix) compensating for bias in the patient airway flow.

19 Claims, 8 Drawing Sheets

(51) Int. Cl.
*A61M 16/06* (2006.01)
*A61M 16/08* (2006.01)

(52) U.S. Cl.
CPC .... *A61M 16/0051* (2013.01); *A61M 16/0057* (2013.01); *A61M 16/06* (2013.01); *A61M 16/0875* (2013.01); *A61M 2016/0036* (2013.01); *A61M 2205/15* (2013.01); *A61M 2205/18* (2013.01); *A61M 2205/3334* (2013.01); *A61M 2230/40* (2013.01)

(58) Field of Classification Search
CPC .......... A61M 16/0051; A61M 16/0057; A61M 16/0069; A61M 16/0875; A61M 2205/15; A61M 2205/18; A61M 2205/14; A61M 2205/3334; A61M 2016/0027; A61M 2016/003; A61M 2016/0036
See application file for complete search history.

(56) References Cited

U.S. PATENT DOCUMENTS

| | | | | |
|---|---|---|---|---|
| 6,000,396 | A * | 12/1999 | Melker | A61M 16/206 128/204.21 |
| 6,142,150 | A * | 11/2000 | O'Mahoney | A61M 16/1065 128/205.18 |
| 6,257,234 | B1 * | 7/2001 | Sun | A61M 16/026 128/204.18 |
| 6,557,553 | B1 * | 5/2003 | Borrello | A61M 16/0051 128/204.18 |
| 6,739,336 | B1 | 5/2004 | Jalde et al. | |
| 9,114,220 | B2 | 8/2015 | Masic | |
| 10,195,391 | B2 | 2/2019 | Cyprowski et al. | |
| 2002/0014240 | A1 * | 2/2002 | Truschel | A61M 16/0051 128/204.22 |
| 2002/0053345 | A1 * | 5/2002 | Jafari | A61M 16/0069 128/204.23 |
| 2002/0059933 | A1 * | 5/2002 | Jaffe | A61M 16/0045 128/204.22 |
| 2006/0084877 | A1 * | 4/2006 | Ujhazy | A61M 16/0066 600/483 |
| 2006/0162728 | A1 * | 7/2006 | Delache | A61M 16/0069 128/204.22 |
| 2007/0144522 | A1 * | 6/2007 | Eger | A61M 16/026 128/205.23 |
| 2007/0157930 | A1 | 7/2007 | Soliman et al. | |
| 2008/0000478 | A1 * | 1/2008 | Matthiessen | A61B 5/085 128/204.23 |
| 2009/0050155 | A1 * | 2/2009 | Alder | A61M 16/06 128/204.23 |
| 2009/0205662 | A1 * | 8/2009 | Kwok | A61M 16/0051 128/204.23 |
| 2009/0241951 | A1 * | 10/2009 | Jafari | A61M 16/026 128/204.21 |
| 2009/0241962 | A1 * | 10/2009 | Jafari | A61M 16/026 128/205.25 |
| 2009/0301486 | A1 * | 12/2009 | Masic | A61B 5/08 128/204.21 |
| 2010/0071696 | A1 * | 3/2010 | Jafari | A61B 5/085 128/204.23 |
| 2010/0101574 | A1 * | 4/2010 | Bassin | A61M 16/0057 128/204.21 |
| 2010/0147303 | A1 * | 6/2010 | Jafari | A61M 16/0051 128/204.23 |
| 2010/0180895 | A1 * | 7/2010 | Kwok | A61M 16/0051 128/204.23 |
| 2010/0218767 | A1 * | 9/2010 | Jafari | A61M 16/0051 128/204.23 |
| 2010/0236553 | A1 * | 9/2010 | Jafari | A61M 16/0816 128/204.21 |
| 2010/0236555 | A1 * | 9/2010 | Jafari | A61M 16/0051 128/204.23 |
| 2011/0146683 | A1 * | 6/2011 | Jafari | A61B 5/085 128/204.21 |
| 2011/0196251 | A1 * | 8/2011 | Jourdain | A61M 16/04 600/538 |
| 2011/0209706 | A1 * | 9/2011 | Truschel | A61M 16/024 128/204.23 |
| 2012/0167885 | A1 * | 7/2012 | Masic | A61M 16/0051 128/204.23 |
| 2012/0215081 | A1 | 8/2012 | Euliano et al. | |
| 2012/0247471 | A1 * | 10/2012 | Masic | A61M 16/0051 128/204.23 |
| 2012/0304997 | A1 | 12/2012 | Jafari et al. | |
| 2013/0118496 | A1 * | 5/2013 | Truschel | A61M 16/026 128/204.23 |
| 2013/0167842 | A1 * | 7/2013 | Jafari | A61M 16/026 128/204.21 |
| 2014/0053840 | A1 * | 2/2014 | Liu | A61M 16/0051 128/204.23 |
| 2014/0194767 | A1 * | 7/2014 | Zheng | A61B 5/03 600/538 |
| 2014/0261409 | A1 * | 9/2014 | Dong | A61M 16/0051 128/202.22 |
| 2014/0288858 | A1 * | 9/2014 | Franklin | G01M 3/2815 702/51 |
| 2015/0000665 | A1 * | 1/2015 | Isaza | A61M 16/026 128/204.23 |
| 2015/0107584 | A1 * | 4/2015 | Jafari | A61M 16/0063 128/202.22 |
| 2015/0174357 | A1 * | 6/2015 | Heck | A61M 16/0051 128/202.22 |

FOREIGN PATENT DOCUMENTS

| | | |
|---|---|---|
| WO | 9806449 A1 | 2/1998 |
| WO | 2010099373 A1 | 9/2010 |
| WO | 2012004718 A1 | 1/2012 |
| WO | 2012004733 A1 | 1/2012 |

\* cited by examiner

METHOD AND SYSTEMS FOR PATIENT AIRWAY AND LEAK FLOW ESTIMATION FOR NON-INVASIVE VENTILATION

CROSS-REFERENCE TO PRIOR APPLICATIONS

This application is the U.S. National Phase application under 35 U.S.C. § 371 of International Application No. PCT/IB2016/054038, filed on Jul. 6, 2016, which claims the benefit of U.S. Provisional Patent Application No. 62/189,522, filed on Jul. 7, 2015 and U.S. Provisional No. 62/232,513 filed on Sep. 25, 2015. These applications are hereby incorporated by reference herein.

FIELD OF THE INVENTION

The present disclosure is directed generally to methods and systems for estimating patient airway flow and leak flow utilizing remote ventilator pressure and flow sensors in a non-invasive ventilator system.

BACKGROUND

The most common means of providing critical care ventilation requires intubating patients with an endotracheal tube that seals within the trachea using an inflatable cuff. Intubation offers the best means of clinically managing the airway and maintaining lung inflation, but it introduce significant risks including tissue abrasion, infection, and sedation of the patient due to extreme discomfort. Accordingly, intubation is appropriately called 'invasive' ventilation, and the clinician's decision to intubate must be carefully considered. For a select group of hospitalized patients requiring breathing support, the risks leading to adverse side effects of intubation can outweigh the benefits.

In light of significant risks of invasive ventilation, a new approach was adopted from home care ventilation that offers the benefit of applying support through the airway, but uses a connection that simply involves fitting a mask over the patient's mouth and nose or uses a tracheostomy tube. This approach is called non-invasive positive pressure ventilation, or simply non-invasive ventilation ("NIV"). For NIV, some leak is expected and often purposely introduced in order to reduce end-tidal $CO_2$ that would otherwise be rebreathed by the patient, since a single limb circuit connects the ventilator to the mask in an NIV system. In comparison, invasive ventilation uses a dual-limb connecting circuit that separately carries exhaled gases, which prevents rebreathing of $CO_2$ in invasive ventilation which therefore requires no leak.

Although the primary function of a ventilator is to provide or supplement patient breathing, ventilators typically include integral monitoring and alarm functions to safeguard the patient and provide essential clinical information. In order to provide these functions, the ventilator monitors waveforms including pressure, flow, and volume. To avoid excess tubing and wires near the patient, and to reduce the risk of occluding the airway with patient secretions, it is desirable not to use an airway flow sensor. Without a proximal flow sensor, sensors inside the ventilator can be used to monitor flow. However, the four to six feet of tubing that separate the ventilator and patient create significant issues with these sensors. Pressure-flow dynamics of the connecting tube, including leak, account for different flow at the patient airway compared to what is measured at the ventilator. Tubing resistance and compliance tend to smooth flow transient, and leak leads to loss of flow at the patient's airway. As a result, flow at the ventilator is a poor estimate of airway flow.

To account for the effect of resistance and compression, ventilator manufacturers apply filtering to waveform measurements using a patient circuit model. These models typically call for the differentiation of the measured pressure, which tends to amplify high frequency noise in the pressure input signal. And since these filters do not involve lung mechanics, the model is incomplete and the airway flow estimate is even more inaccurate.

Accordingly, there is a need in the art for non-invasive ventilator systems that properly estimate patient airway flow and leak flow utilizing remote ventilator pressure and flow sensors.

SUMMARY OF THE INVENTION

The present disclosure is directed to inventive methods and systems for estimating patient airway flow in a non-invasive ventilator system. Various embodiments and implementations herein are directed to a non-invasive ventilator system that calculates a highly accurate estimate of patient airway flow and of unknown leak flow. The non-invasive ventilator uses a feedback mechanism to minimize the difference between measured proximal pressure and estimated proximal pressure, where the estimated proximal pressure is generated using a model of the patient circuit that connects the ventilator with the patient. The non-invasive ventilator also compensates for leaks that can occur in the system by adjusting a known leak flow estimate.

Generally in one aspect, a method for estimating patient airway flow in a non-invasive ventilator system is provided. The method includes the steps of: (i) providing a non-invasive ventilator system having tubing with a distal, ventilator end and a proximal, patient end; (ii) obtaining a measurement of tubing compliance and a measurement of one or more parameters of an exhalant port leak flow model of the non-invasive ventilator system; (iii) measuring, using one or more distal gas flow sensors of the non-invasive ventilator, gas flow at the distal end of the tubing; (iv) measuring, using a proximal pressure sensor of the non-invasive ventilator, pressure at the proximal end of the tubing; (v) determining an estimated gas flow at the proximal end of the tubing, the estimated gas flow calculated from the measurement of gas flow at the distal end of the tubing, the measurement or pressure at the proximal end of the tubing, the obtained measurement of tubing compliance, and the obtained measurement of one or more parameters of the leak flow model; (vi) determining a proximal pressure error value by subtracting the measured pressure at the proximal end of the tubing from the estimated pressure at the proximal end of the tubing; (vii) compensating, using a compensator, for the determined proximal pressure estimate error value; (viii) compensating for an error in the estimated gas flow at the proximal end of the tubing by feeding that estimate back into a sum of accumulated flows; (ix) determining an estimated gas flow leak, the estimated gas flow leak calculated from the estimated pressure at the proximal end of the tubing and the obtained measurement of one or more parameters of the leak flow model; (x) monitoring for an unknown leak in the non-invasive ventilator system; (xi) determining, when an unknown leak is identified, a gas flow leak factor; (xii) adjusting, with the determined gas flow leak factor, the estimated gas flow leak; and (xiii) compensating for bias in the patient airway flow.

According to an embodiment the step of obtaining a measurement of tubing compliance and a measurement of one or more parameters of the leak flow model includes one or more calibration measurements.

According to an embodiment, the method further includes the step of comparing the gas flow leak factor to a predetermined lower limit.

According to an embodiment, an alarm is triggered if the gas flow leak factor is below the predetermined lower limit.

According to an embodiment, the method further includes the step of comparing the gas flow leak factor to a predetermined upper limit.

According to an embodiment, an alarm is triggered if the gas flow leak factor is above the predetermined upper limit.

According to an embodiment, the compensator is a proportional-integral compensator.

Generally, in one aspect, a non-invasive ventilator system is provided. The system includes: airway tubing having a distal, ventilator end and a proximal, patient end; a distal gas flow sensor configured to measure gas flow at the distal end of the tubing; a proximal pressure sensor configured to measure pressure at the proximal end of the tubing; and a gas flow controller configured to supply a determined volume of gas to the distal end of the tubing, wherein the gas flow controller is configured to determine the supplied volume of gas by: (i) determining an estimated gas flow at the proximal end of the tubing, the estimated gas flow comprising a measurement of gas flow at the distal end of the tubing, a measurement of pressure at the proximal end of the tubing, a measurement of tubing compliance, and a measurement of one or more parameters of a leak flow model; (ii) determining a proximal pressure error value by subtracting a measured pressure at the proximal end of the tubing from the estimated pressure at the proximal end of the tubing; (iii) compensating for the determined proximal pressure estimate error value; (iv) compensating for an error in the estimated gas flow at the proximal end of the tubing by feeding that estimate back into a sum of accumulated flows; (v) determining an estimated gas flow leak, the estimated gas flow leak comprising the estimated pressure at the proximal end of the tubing and the obtained measurement of one or more parameters of the leak flow model; (vi) monitoring for an unknown leak in the non-invasive ventilator system; (vii) determining, when an unknown leak is identified, a gas flow leak factor; (viii) adjusting, with the determined gas flow leak factor, the estimated gas flow leak; and (ix) compensating for bias in the patient airway flow.

According to an embodiment, the controller includes a compensator configured to compensate for the determined proximal pressure estimate error value.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of a non-invasive ventilator ("NIV") system and method. More generally, Applicants have recognized and appreciated that it would be beneficial to provide an NIV that accurately estimates patient airway flow and leak flow utilizing remote ventilator pressure and flow sensors. For example, the NIV uses feedback control to minimize the difference between measured and estimated proximal pressure, where the estimated pressure is synthesized using a model of the patient circuit that connects the ventilator with the patient. Unexpected or unknown leaks that occur during use are compensated using a feedback mechanism that modifies net flow to zero by adjusting a known leak estimate. The method and system results in an airway flow estimate that closely tracks true airway flow with low noise and minimum bias, and provides an accurate estimate of the unknown leak flow.

Although the method and system described below is applied to an NIV, the methods could similarly be utilized to manage the movement of compressible gas through any conveying channel, such as for heating and/or air conditioning systems. Essentially any system that contains a need to remotely estimate flow could utilize the methods and systems described or otherwise envisioned herein.

Figure 1:
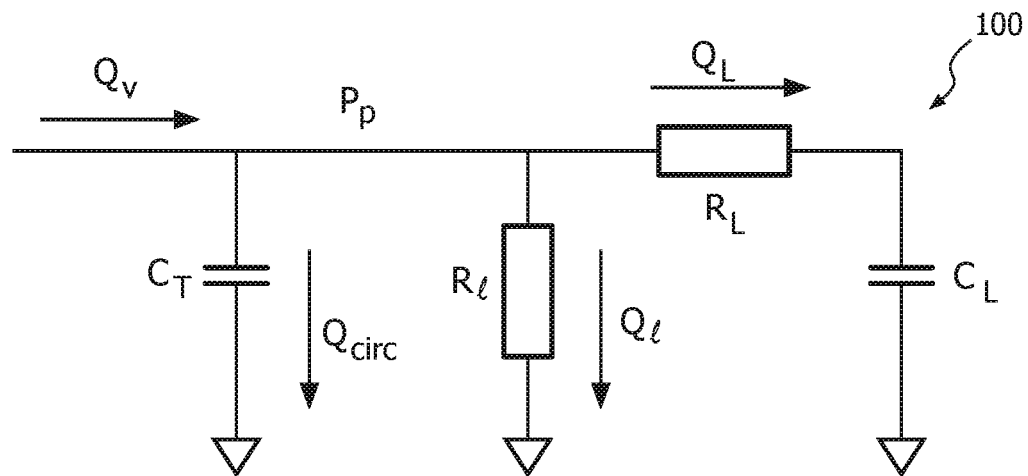
FIG. 1 is a schematic representation modeling flows and pressures in a patient-connected non-invasive ventilator system, in accordance with an embodiment.

Referring to FIG. 1, in accordance with an embodiment, is a model for an NIV system 100 using an electrical circuit analogy where branch currents represent flows, nodal voltages represent pressures, capacitance represents pneumatic compliance, and electrical resistance, flow restriction. In FIG. 1, $Q_v$ is the measured net flow into tubing from the ventilator; $C_T$ is the measured compliance of the tubing; $Q_{circ}$ is the flow component stored in tubing compliance during compression; $P_p$ or $P_{prox}$ is the measured pressure at the proximal side of the airway; $R_l$ is the measured Port leak resistance; $Q_l$ is the flow component lost to ambient through the port leak; $Q_L$ is the unknown flow component into the lung; $R_L$ is the unknown nonlinear lumped airway resistance; and $C_L$ is the unknown lumped compliance of the lung. The set of equations that model the circuit in FIG. 1 and relate pressures and flows, if interpreted directly for a solution of the lung flow result in a non-causal form requiring that the noisy proximal pressure signal be differentiated. But then the patient circuit is not in isolation, but rather coupled to the patient's lung which, if these dynamics are considered, results in a smoothing of the derivative. The coupled model depicted in FIG. 1 also results in tangling between circuit and lung parameters, which is not difficult to untangle in estimation if the system was linear, but the nonlinear resistance parameters makes untangling impossible—the resulting quadratic differential equation is intractable and so the lung resistance and compliance cannot be estimated by typical means.

Figure 3:
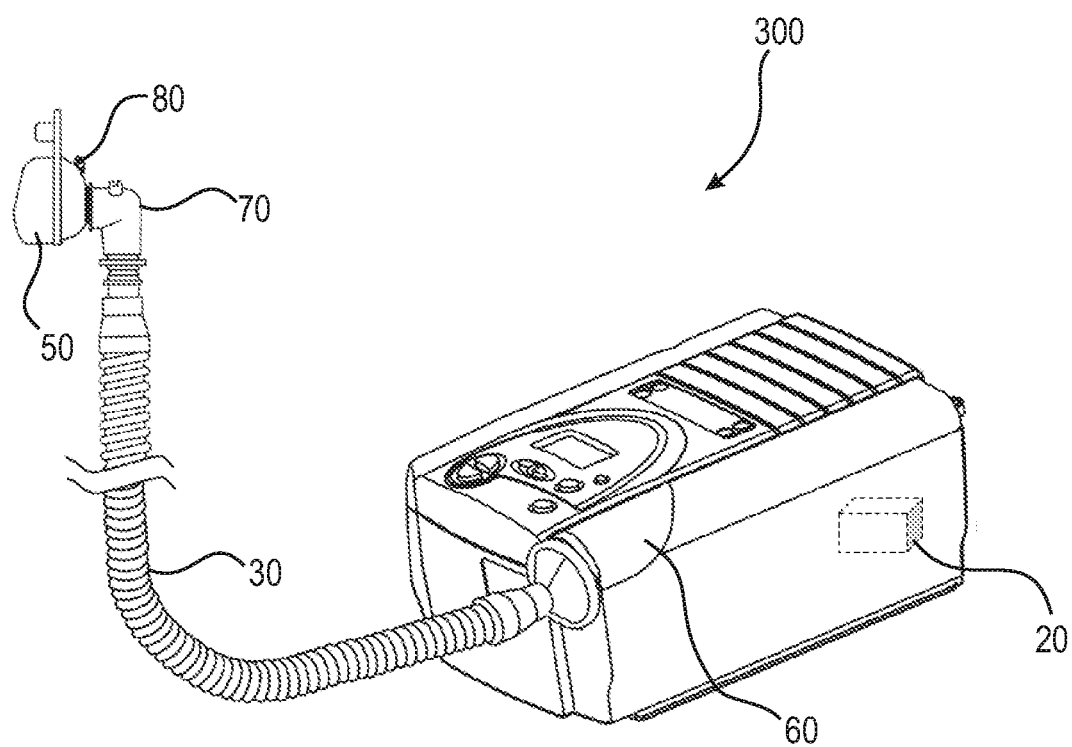
FIG. 3 is a schematic representation of a non-invasive ventilator system in accordance with an embodiment.

In view of the foregoing, various embodiments and implementations are directed to an NIV that estimates patient airway flow and leak flow with feedback mechanisms that utilize remote ventilator pressure and flow sensors. Referring to FIG. 3, in one embodiment, is a representation of an example NIV system 300. The NIV includes a gas source which can be any gas utilized for breathing, including but not limited to atmospheric air and oxygen, among others. The gas source is expelled from the NIV with a predetermined pressure. The NIV also includes a controller 20, which is a conventional microprocessor, an application specific integrated circuit (ASIC), a system on chip (SOC), and/or a field-programmable gate arrays (FPGA), among other types of controllers. A controller may be implemented with or without employing a processor, and also may be implemented as a combination of dedicated hardware to perform some functions and a processor (e.g., one or more programmed microprocessors and associated circuitry) to perform other functions.

The controller 20 can be coupled with or otherwise in communication with any needed memory, power supply, I/O devices, control circuitry, and/or other devices necessary for operation of the NIV according to the embodiments described or otherwise envisioned herein. For example, in various implementations, a processor or controller may be associated with one or more storage media. In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

The NIV includes a tube or tubing 30 that delivers gas from the remote ventilator component 40 to the user interface 50. User interface 50 can be, for example, a face mask that covers all or a portion of the user's mouth and/or nose. There may be masks of many different sizes to accommodate patients or individuals of different sizes, and/or the mask may be adjustable. As another alternative, user interface 50 may fit within or on, or otherwise interact with, a tracheostomy tube. Accordingly, the user interface 50 may be a variety of sizes to accommodate tracheostomies of different shapes and sizes. The user interface is configured to fit with at least a portion of the patient's airway and includes an exhalation port 80. The NIV system comprises a distal gas flow sensor 60 at the end of the tubing near the remote ventilator component 40, and a proximal pressure sensor 70 at the end of the tubing near the user interface 50. Either of distal gas flow sensor 60 or proximal pressure sensor 70 may comprise, for example, two or more sensors. For example, distal gas flow sensor 60 can comprise a blower flow sensor and an $O_2$ valve sensor. Further, any of the sensors may be external or internal to the NIV. Controller 20 is configured to receive sensor data from both distal gas flow sensor 60 and proximal pressure sensor 70, either through wired or wireless communication.

Notably, proximal pressure sensor 70 is located at the output of tubing 30 rather than in close proximity to the patient or individual's mouth. Accordingly, the data obtained by proximal pressure sensor 70 is not directly equivalent to gas flow in the patient airway, and an estimate of airway flow is necessary. One method used to estimate patient airway flow ($Q_L$) is via the following equation:

$$\hat{Q}_L = Q_v - C_T \frac{dP_p}{dt} - \text{sgn}(P_p)\sqrt{\left|\frac{P_p}{R_l}\right|} \qquad (1)$$

where $\hat{Q}_L$ is estimated patient airway flow, $Q_v$ is the gas flow as measured by the distal gas flow sensor 60, $C_T$ is the patient connecting circuit compliance, $P_p$ is the gas flow as measured by the proximal pressure sensor 70, and $R_l$ is the total leak resistance. However, equation (1) results in a noisy airway flow estimate and large transient errors. This is largely due to the second term in the equation which accounts for flow lost to compression of gas in the patient circuit and the derivative of a noisy pressure signal. To compensate for noise the estimate is usually filtered, but this leads to additional error if the filter is not selected correctly to match patient lung dynamics.

Figure 2:
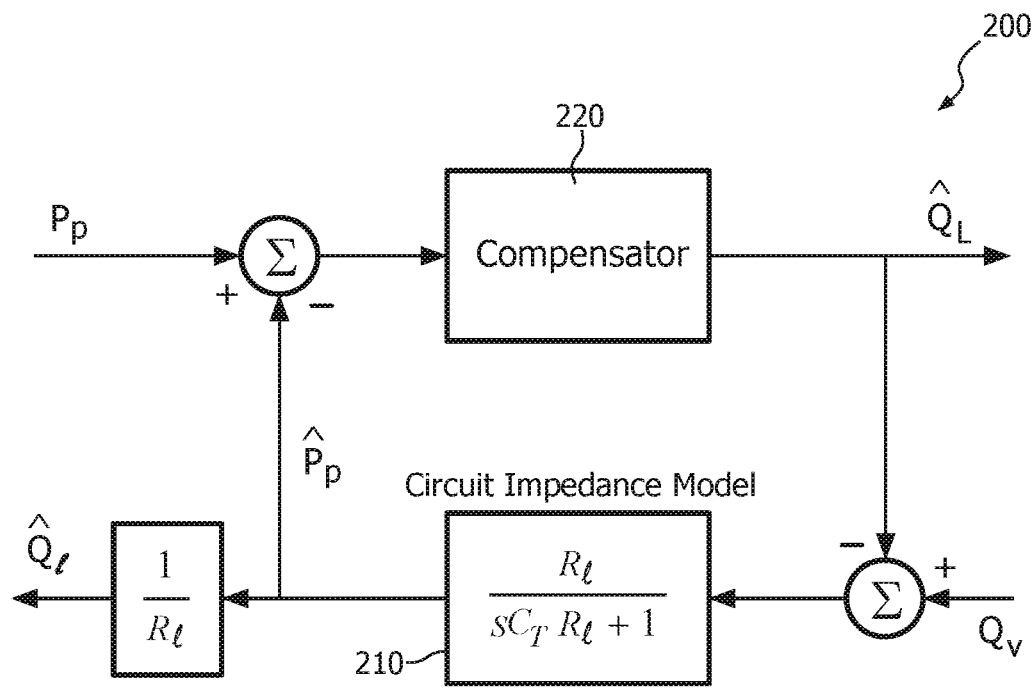
FIG. 2 is a schematic representation of a model for estimating patient airway flow in a non-invasive ventilator system, in accordance with an embodiment.

Referring to FIG. 2, in one embodiment, is a schematic of a ventilator/patient circuit 200 for estimating patient airway flow in a non-invasive ventilator system. The circuit comprises a measured distal gas flow $Q_v$ which is the gas flow input into the circuit, a circuit impedance model 210 which uses measures of the leak resistance and circuit compliance to the gas flow, an estimate of $Q_l$ which is the connecting circuit leak flow (which utilizes the total leak resistance $R_l$), the proximal pressure $P_p$ as measured by the proximal pressure sensor 70, a compensator 220, and the estimated patient airway flow $\hat{Q}_L$. According to an embodiment, the pressure synthesized by the connecting circuit impedance model 210 is an estimate of the proximal pressure based on a sum of net flows into the circuit impedance. This is subtracted from the measured pressure and the difference between measured and estimated pressures is minimized by the controller 20. By choosing a suitable compensator 220, the controller output is effectively driven to approach a close estimate of the airway flow ($\hat{Q}_L$) to complete a feedback loop. According to an embodiment, a proportional-integral compensator ("PI compensator") is utilized to drive the difference between the proximal pressure measurement and its estimate to zero and thus the estimates of the airway and leak flows. According to an embodiment, the PI compensator utilizes the following equation:

$$\hat{Q}_L = \left(\frac{K_i + K_p s}{s}\right)(P_p - \hat{P}_p) \qquad (2)$$

where $K_i$ is the integral gain and $K_p$ the proportional gain. Although a PI compensator can be utilized, many other compensators that provide loop stability and suitably cause the error to converge towards zero—therefore causing $\hat{P}_p$ to track $P_p$ can similarly be used.

Airway Flow Analysis

According to an embodiment, therefore, the NIV model in FIG. 1 can be expanded to a nonlinear, linear parameter varying model. The nonlinear equations that approximate the coupled NIV-patient circuit with the patient are then:

$$P_{prox} = \frac{1}{C_T} \int (Q_v - Q_l - Q_L) dt \quad (3)$$

$$P_{prox} - P_L = R_L Q_L^2 \text{sgn}(Q_L) \quad (4)$$

$$P_{prox} = R_l Q_l^2 \text{sgn}(Q_l) \quad (5)$$

$$P_L = \frac{1}{C_L} \int Q_L dt \quad (6)$$

Figure 4:
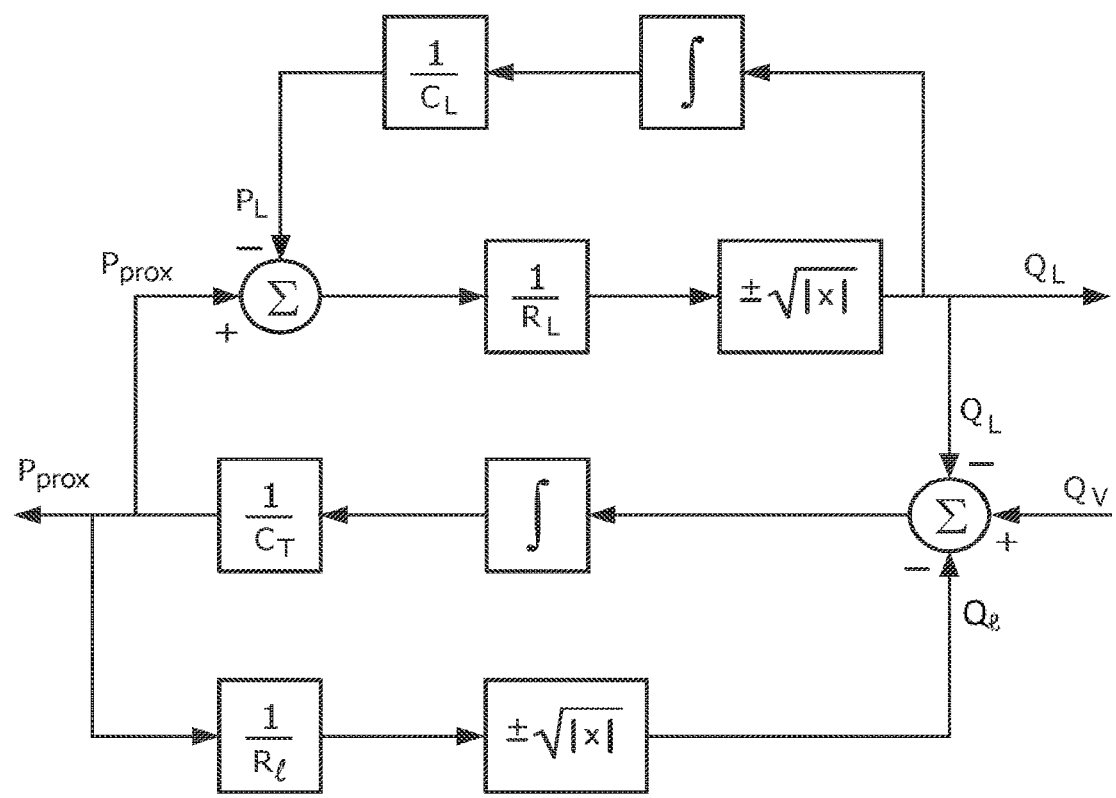
FIG. 4 is schematic representation modeling flows and pressures in a patient-connected non-invasive ventilator system, in accordance with an embodiment.

This set of equations can be expressed as a block diagram, as illustrated in FIG. 4. The upper portion of FIG. 4 depicts the portion of the model involving the lung, and the lower portion of FIG. 4 depicts the patient circuit. The two portions couple to one another through the proximal pressure, $P_{prox}$ and lung flow, $Q_L$. If patient circuit resistance is not considered the ventilator outlet flow only can be used as a measurable input, and the machine pressure offers no further useful information. $Q_l$ is the net leak flow, determined by $P_{prox}$ and the leak flow model (shown as, for example, $R_1$ in FIG. 4, although other models are possible). The output to determine is $Q_L$. Although $Q_L$ is not measured, the proximal airway pressure, $P_{prox}$ is measured. $P_L$ is the lung pressure, and $C_L$ and $R_L$ are the lung compliance and resistance respectively. It is typically assumed that both $C_T$ and the leak model are known, and according to one embodiment can be determined from a pre-use calibration procedure on the circuit, among other mechanisms.

Figure 5:
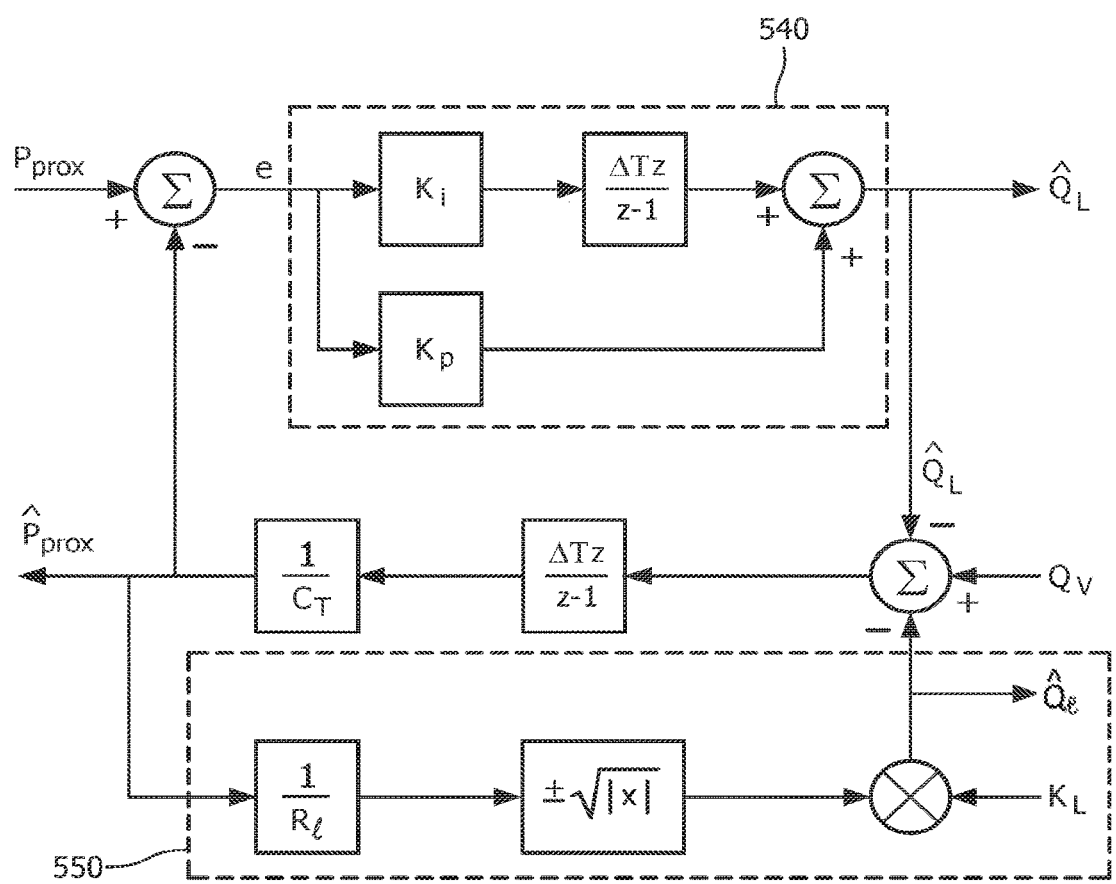
FIG. 5 is schematic representation of a model for estimating patient airway flow in a non-invasive ventilator system, in accordance with an embodiment.

According to an embodiment, since there is difficulty in determining $R_L$ and $C_L$, this part of the model can be eliminated and replaced by a discrete time filter if other adjustments are also made. Additionally, the known part of the model can be replaced by a discrete time equivalent of the original continuous time model as illustrated in FIG. 5. The filter replaces the portion of the model depicted in FIG. 4 that represented the lung, but it does not simulate the lung. The output of the circuit portion of the model that determines $P_{prox}$ is now treated as an estimate of $P_{prox}$ ($\hat{P}_{prox}$), and this value is subtracted from the actual measured $P_{prox}$. This difference, e, becomes the input to the filter. The integral action of the filter acts to minimize e, by the action of its output that acts on the circuit part of the model, feeding back into where $Q_L$ once connected. But $Q_L$ is now treated as an estimate and so designated as $\hat{Q}_L$. By selecting the filter parameters $K_i$ and $K_p$, the overall feedback system can be stabilized and e can be made to converge to zero. With rapid convergence, $\hat{P}_{prox}$ will track the measured $P_{prox}$ and this will cause $\hat{Q}_L$ and $\hat{Q}_l$ to track the actual lung and leak flow (provided the actual $R_1$ is correct).

Leak Disturbance Compensator

When unknown or unexpected leaks occur within the NIV system, additional control is required in order to ensure convergence of the estimated leak and lung flows. Although no further information can be derived on a sample by sample basis, there is information over a full breath cycle that can be used to determine if there is unexpected leak flow in the circuit-lung system. At steady state settings of breath rate and inspiratory time, the volume that enters the lung during inhalation must equal the volume that exits the lung during exhalation. It can be assumed under most conditions that any difference between these volumes can be attributed to volume loss not accounted for by the fixed leak models. Therefore the leak flow estimate can be adjusted by multiplying by a factor over the breath cycle. This also assumes that the unknown leak is somewhat stationary over the period of a breath cycle or is at least changing slowly. Additionally, according to an embodiment, the leak factor ($K_L$) which is fixed at a value at the start of every breath, and based on reconciliation of leak from the prior breath, multiplies the output of the known leak to get $\hat{Q}_l$ before feeding back into the estimator. Thus, $\hat{Q}_l$ becomes the total leak, including both the known and unknown components.

The manner in which $K_L$ is determined requires careful consideration of how the net breath volume is processed since there is a one-breath delay dynamic involved, and improper management can lead to too slow of a convergence, hunting, limit cycles or even instability in the estimator. Graphical root locus synthesis was used to derive such a controller, based on the model, $Kz^{-1}$. K is the sensitivity of average total leak flow to change in $K_L$, which averages about 0.4 liters/sec, however is sensitive to the fixed leak and breath parameters. And the one sample delay comes by looking back one sample (one breath). The leak factor is limited between zero and a maximum expected leak flow. If there is no leak flow beyond what is expected from the mask and exhalation port, the output of the controller should converge to a number very close to 1. By allowing the factor to go lower than 1, in this design all the way to zero, the controller can correct for unexpected or unknown leak flow resistances that were underestimated, or if for any reason the port leak or mask leak were to become blocked during operation.

Figure 6A:
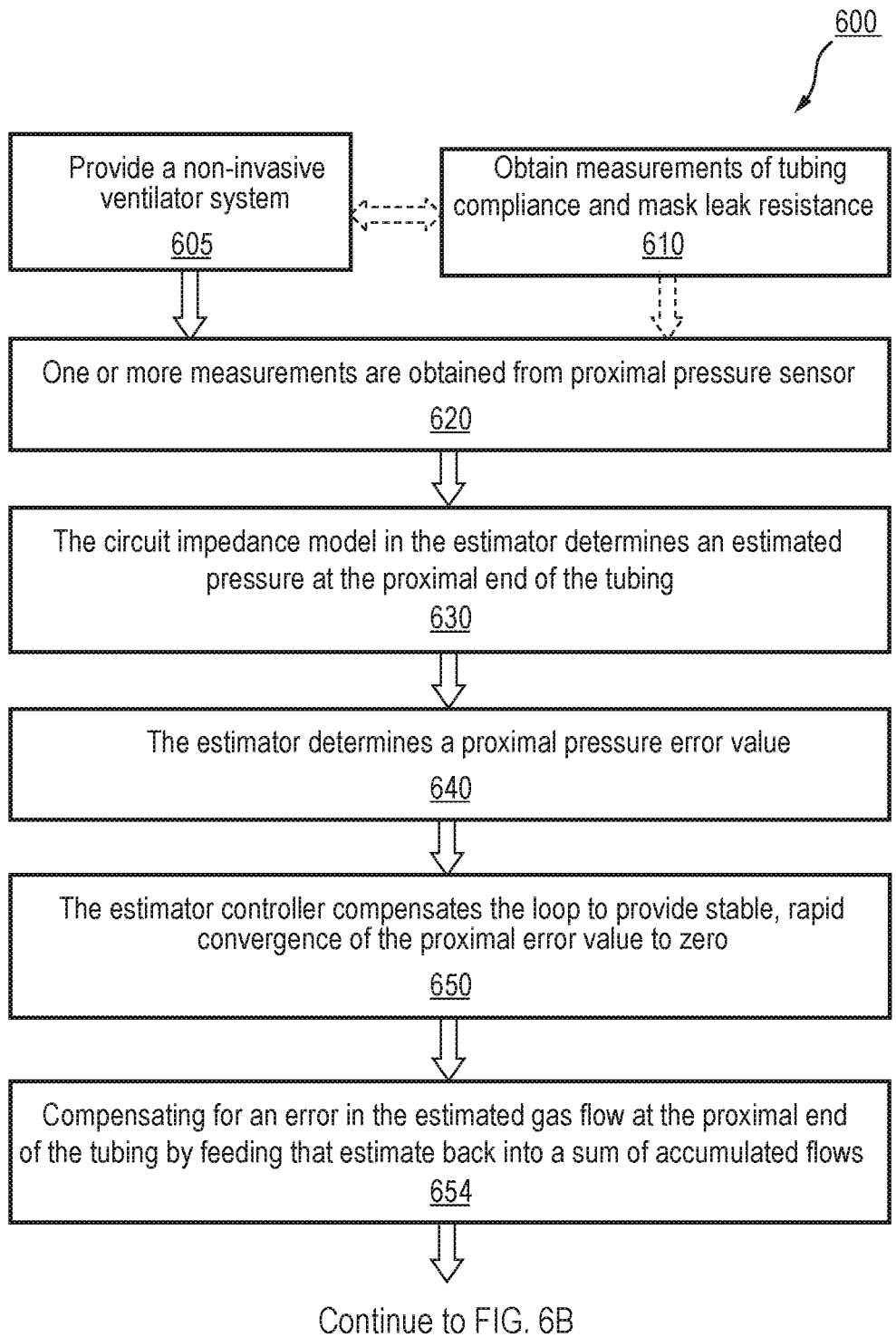
FIG. 6A is a flowchart of a method for estimating patient airway flow in a non-invasive ventilator system, in accordance with an embodiment.
Figure 6B:
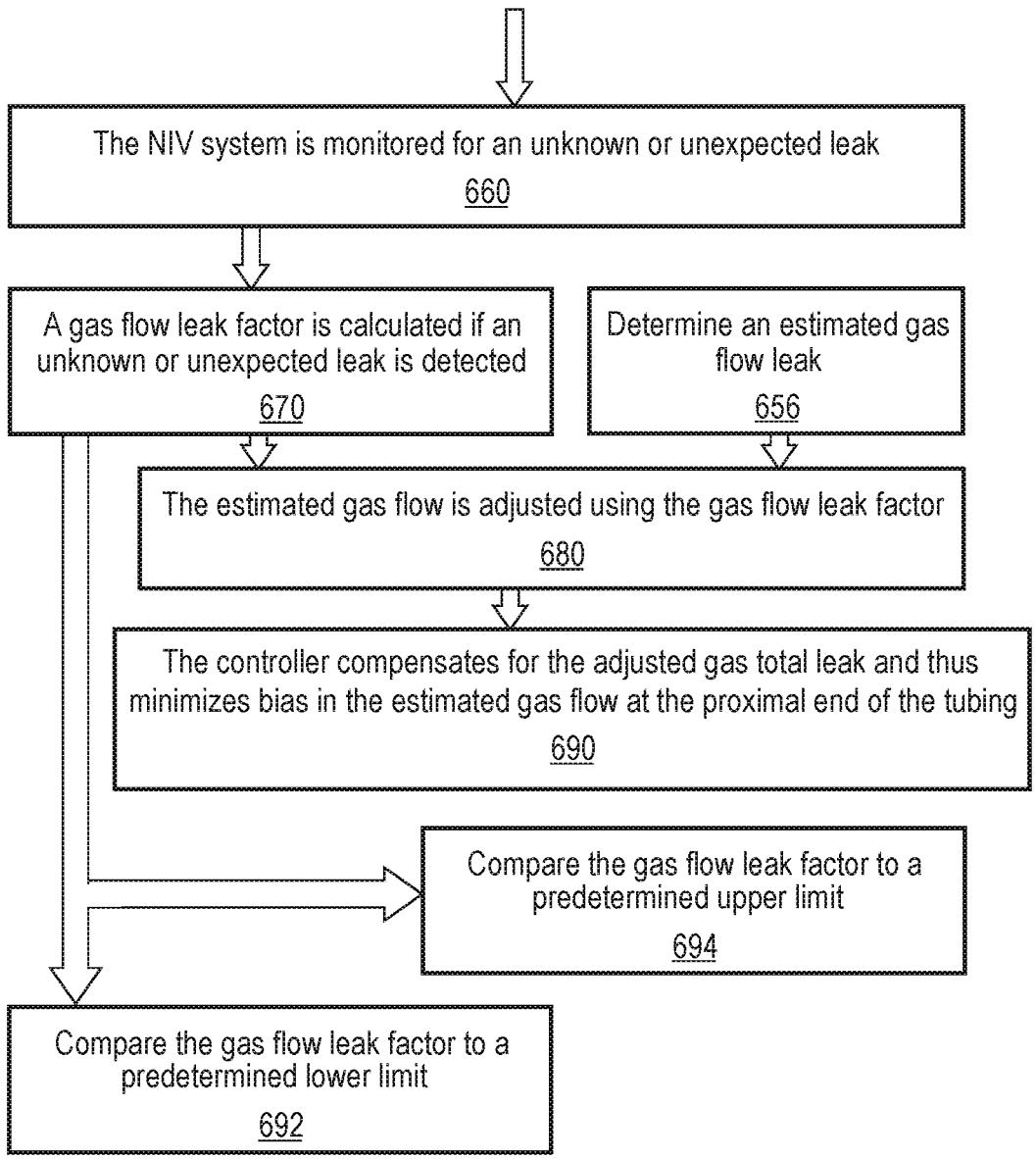
FIG. 6B is a flowchart of a method for estimating patient airway flow in a non-invasive ventilator system, in accordance with an embodiment.

Referring to FIGS. 6A and 6B, in one embodiment, is a flowchart of a method 600 for estimating patient airway flow in a non-invasive ventilator system. At step 605, an NIV system is provided. The NIV system can be any of the embodiments described or otherwise envisioned herein. At step 610, measurements of tubing compliance ($C_T$) and leak resistance ($R_1$) are retrieved or obtained. These measurements are typically obtained during patient setup prior to breath delivery. For example, according to one embodiment the value of $R_1$ is determined based on a calibration procedure. Alternatively, $R_1$ can be retrieved from a database of $R_1$ values, where the values can depend on the user selecting tubing set and/or port leak part numbers from a user screen interface, automatically using an RFID tag implanted in the tubing set or its components, a bar scanning system that reads the part numbers into the ventilator, or a variety of other methods. Tubing compliance ($C_T$), for example, affects the amount of gas compressed in the ventilator circuit according to the pressure generated by the ventilator throughout the breath. The compressible volume can vary depending on the internal volume of the circuit and stiffness of its wall.

At step 620 of the method, one or more measurements are obtained from proximal pressure sensor 70 at the end of the tubing proximal the user interface 50. The proximal pressure sensor 70 can obtain the measurement(s) of pressure using any of a variety of measurement methods and devices.

At step 630 of the method, the controller 20 determines an estimated pressure ($P_{prox}$) at the proximal end of the tubing. Estimation of pressure at the proximal end of the tubing utilizes one or more obtained measurements of gas flow ($Q_v$) at the distal end of the tubing, as well as the obtained measurement of tubing compliance ($C_T$) and leak resistance.

At step 640 of the method, the controller 20 determines a proximal pressure estimate error value (e) by subtracting the actual measured proximal pressure ($P_{prox}$) from estimated proximal pressure ($\hat{P}_{prox}$). At step 650 of the method, the controller 20 minimizes the pressure error using a proportional-integral compensator. As shown for example, in FIG. 5, according to an embodiment, the calculated difference e is utilized as an input to filter 540. The integral action of the filter acts to minimize e, by the action of its output that acts on the circuit part of the model, feeding back into where $Q_L$ once connected. But $Q_L$ is now treated as an estimate and so designated as $\hat{Q}_L$. By selecting the filter parameters $K_i$ and $K_p$ by either analytical methods or ad-hoc tuning, the overall feedback system can be stabilized and e can be made to rapidly converge and remain near zero. With the convergence, $\hat{P}_{prox}$ will track the measured $P_{prox}$ and this will cause $\hat{Q}_L$ and $\hat{Q}_l$ to track the actual lung and leak flow—provided the leak model, its parameters, and the compliance are correct. When additional 'unknown' leaks occur or $R_1$ was perhaps determined with an error, the system requires further control measures to assure convergence of the estimated leak and lung flows, and bias, as discussed in greater detail below. According to an embodiment, the measurements and/or calculations obtained throughout the course of the method can be obtained and/or updated periodically or continually.

At step 654 of the method, the controller causes errors in the obtained estimate of the patient airway flow to become small by providing the estimate back into the sum of accumulated flows.

At step 656 of the method, an estimated gas flow leak is calculated. The estimated gas flow leak is based on the estimated pressure at the proximal end of the tubing and the leak model with parameters obtained apriori. Like several other steps of the method, this step can occur before, after, or simultaneously with other steps.

At step 660 of the method, the NIV system is monitored for an unknown or unexpected leak. The circuit impedance model described herein includes a leak model for estimating leak behavior, but this leak is intentionally built into the circuit (such as for patient exhalation through exhalation port 80. This leak value is assumed not to change, and is typically calibrated or known prior to patient connection. During the application of ventilation, additional unknown or unexpected leaks can develop, for example around the mask skirt sealing the mask against the patient's face. Unknown leak can be treated as disturbance in the system, and the size estimated during ventilation using a feedback controller that is the same or separate from controller 20. According to an embodiment, the feedback controller acts to minimize the integrated, estimated airway flow, $\hat{Q}_L$, over a full breath. This is equivalent to minimizing the net estimated lung volume for each breath. If net estimated lung volume is reduced to zero, there is no leak component in the average flow that was integrated to get the volume. Any residual volume acts in a breath-to-breath feedback control law to adjust a correcting factor, $K_l$, which corrects the output of the leak model.

Accordingly, at step 670 of the method, the gas flow leak factor $K_L$, is calculated. At step 680 of the method, the estimated gas flow is adjusted using the gas flow leak factor $K_L$, and at step 690 of the method, the controller 20 compensates for the adjusted gas total leak. Referring to FIG. 5, according to one embodiment, the leak disturbance model 550 calculates a correcting factor $K_L$ which is then utilized to correct the output of the leak model. Accordingly, compensating for the adjusted gas total leak compensates for bias in the patient airway flow. In other words, minimizing the difference between the estimated inspired gas volume and the exhaled gas volume—or equivalently forcing net estimated volume to zero—minimizes bias in the airway flow estimate.

At optional step 692 of the method, the gas flow leak factor is compared to a predetermined lower limit. If the gas flow leak factor is below the predetermined lower limit, then a low leak or fault condition of the exhalant port is determined. A warning, alarm, or gas flow adjustment can then occur depending on the settings and/or programming of the NIV system. The lower limit can be a factory setting, an adjustable setting, and/or a setting that depends on factors such as the patient's size, condition, illness, and more, among many other factors.

At optional step 694 of the method, the gas flow leak factor is compared to a predetermined upper limit. If the gas flow leak factor is above the predetermined upper limit, then a disconnect fault of the patient tubing is determined. A warning, alarm, or gas flow adjustment can then occur depending on the settings and/or programming of the NIV system. The upper limit can be a factory setting, an adjustable setting, and/or a setting that depends on factors such as the patient's size, condition, illness, and more, among many other factors. Among many other things, these limits can detect $CO_2$ build-up and a possible circuit disconnect.

Estimator Calculations

According to an embodiment the estimator comprises a filter that minimizes the difference between measured and estimated $P_{prox}$, and the circuit dynamic model section. The calculations can be updated every control cycle, although other time frames are possible. The filter section can comprise, for example, the following:

$$\hat{e}_{QL}(n) = -P_{prox}(n) + \hat{P}_{prox}(n) \quad (7)$$

$$I_{Fin}(n) = \hat{Q}_{LKi}\hat{e}_{QL}(n) - I_{Fout}(n) - \hat{Q}_{LKp}\hat{e}_{QL}(n) + \hat{Q}_L(n) \quad (8)$$

$$\hat{Q}_L(n) = \min\{\max\{(I_{Fout}(n) - \hat{Q}_{LKp}\hat{e}_{QL}(n)), Q_{Lmin}\}, Q_{Lmax}\} \quad (9)$$

$$I_{Fout}(n) = \begin{cases} 0 & \text{if } Q_{Lreset} = 1 \\ \Delta T \cdot I_{Fin}(n-1) + I_{Fout}(n-1) & \text{otherwise} \end{cases} \quad (10)$$

where, according to an embodiment, $I_{Fout}(0)=I_{Fin}(0)=0$; $Q_{Lmin}=Q_{Lmax}=-5.0$ lps; 5.0 lps; $\hat{Q}_{LKi}=10.0$ liters/(sec$^2$ cm $H_2O$); and $\hat{Q}_{LKp}=0.3$ liters/(sec cm $H_2O$).

According to an embodiment, overall negative feedback is accomplished in the estimator loop no matter which order the difference between proximal pressure measure and estimate are taken. According to this embodiment, an odd number of negative signs are required in the loop. For example, when the pressure error is written as $P_{prox}-\hat{P}_{prox}$, the compensator equations must include a sign inversion since $\hat{Q}_L$ feeds back into the sum of flows with a negative sign. According to an embodiment, this negative feedback is required for stable estimator operation.

According to an embodiment, the estimator circuit dynamic model section can comprise, for example, the following:

$$Q_{sum}(n) = \frac{1}{60}(Q_b(n) + Q_{O2}(n)) - \hat{Q}_L(n) - \hat{Q}_l(n) \quad (11)$$

-continued $$I_{Cin}(n) = Q_{sum}(n) + Q_{La}(n) \quad (12)$$

$$C_T = C_{Tcal} \quad (13)$$

$$Q_{La}(n) = \hat{P}_{prox}(n) - \frac{1}{C_T} I_{Cout}(n) \quad (14)$$

$$\hat{P}_{prox}(n) = \min\left\{\max\left\{\frac{1}{C_T} I_{Cout}(n), P_{proxMin}\right\}, P_{proxMax}\right\} \quad (15)$$

$$I_{Cout}(n) = \begin{cases} 0 & \text{if } Q_{Lreset}(n) = 1 \\ \Delta T \cdot I_{Cin}(n-1) + I_{Cout}(n-1) & \text{otherwise} \end{cases} \quad (16)$$

$$\hat{Q}_l(n) = K_L(k)[Q_{Lmask}(n) + Q_{Lport}(n)] \quad (17)$$

$$Q_{Lport}(n) = \frac{1}{2K_{2port}}\left(\sqrt{4.0 K_{2port} \max\{0, \hat{P}_{prox}(n)\} + K_{1port}^2} - K_{1port}\right) \quad (18)$$

$$Q_{Lmask}(n) = \begin{cases} 0 & \text{if } MaskLeakType = \text{'other'} \\ \sqrt{\left|\frac{\hat{P}_{prox}(n)}{R_{lmask}}\right|} * \text{sgn}(\hat{P}_{prox}(n)) & \text{otherwise} \end{cases} \quad (19)$$

According to an embodiment, equation (18) assumes that the port leak flow is always positive; the quadratic model assumes $\hat{P}_{prox}(n) > 0$ and therefore the model does not include sign correction. $K_L$, determined by the output of the unknown leak compensation controller is indexed by the breath rate (index k) and updated at the start of every breath. So its value reflects information from the previous breath, applied to the current breath.

The value of $R_{lmask}$ is known based on apriori calibration data of the mask and categorized according to MaskLeak-Type, which is selected during patient setup, prior to breath delivery. TABLE 1 below provides the values of $R_{lmask}$ according to the selected MaskLeakType.

TABLE 1

Values of $R_{lmask}$ According to the Selected MaskLeakType.

| MaskLeakType | $R_{lmask}$ (cm H$_2$O)/lps$^2$ |
| --- | --- |
| 1 | 1420 |
| 2 | 52 |
| 3 | 37 |
| 4 | 24 |
| 'other' | 1 (Dummy value) |

According to an embodiment, $K_{2port}$ (cm H$_2$O/lps$^2$), $K_{1port}$ (cm H$_2$O/lps) and $C_{Tcal}$ (liters/cm H$_2$O) are all measured during the patient circuit calibration procedure before breath delivery starts. For useful output the estimates are filtered and scaled to units of lpm.

First order filters are utilized to filter non-useful high frequency signal and to scale the flow in units of lpm. The general continuous time (LaPlace) form of this filter is:

$$y(s) = \frac{as + b}{cs + d} x(s) \quad (20)$$

and the continuous filter is approximated using any of the discrete time substitutions, and in this particular embodiment, Tustin's bilinear transformation:

$$\frac{2}{\Delta T} \frac{z-1}{z+1} \to s \quad (21)$$

TABLE 2

Filtered Flow Definitions for NIV

| Lung flow | Total leak Flow | Port leak Flow | Mask leak Flow |
| --- | --- | --- | --- |
| $x(n) = \hat{Q}_L(n)$ | $x(n) = \hat{Q}_l(n)$ | $x(n) = Q_{Lport}(n)$ | $x(n) = Q_{Lmask}(n)$ |
| a = 0.0 | a = 0.0 | a = 0.0 | a = 0.0 |
| b = 1.0 | b = 1.0 | b = 1.0 | b = 1.0 |
| c = 0.005 sec | c = 0.005 sec | c = 0.005 sec | c = 0.005 sec |
| d = 1.0 | d = 1.0 | d = 1.0 | d = 1.0 |
| $\Delta T$ = 0.001 sec | $\Delta T$ = 0.001 sec | $\Delta T$ = 0.001 sec | $\Delta T$ = 0.001 sec |
| $\hat{Q}_{LNIV}(n) =$ 60y(n) | $\hat{Q}_{ltotal}(n) =$ 60y(n) | $Q_{lport}(n) =$ 60y(n) | $Q_{lmask}(n) =$ 60y(n) |

According to an embodiment, when either standby, circuit disconnect, or emergency ventilation conditions occur, $Q_{Lreset}$ can be set. This flag resets or holds the estimator functions at their initial conditions until breath delivery is restored. Reset affects the core estimator, the unknown leak compensation controls, and the net lung volume calculations and is used to suspend estimation when either inlet flows or proximal pressure measurements can no longer be obtained, or where the system determines the circuit model behavior has been compromised.

$$Q_{Lreset}(n) = \text{NIVStandby}(n) \text{ OR NIV\_Circ\_Disconnect}(n) \quad (22)$$

In the event that proximal pressure can no longer be measured (e.g. from a sense line disconnect), algorithms can be used to sense this condition, and in that case substitute an alternate proximal pressure estimate that can substitute for the measurement based on the inlet circuit flow, the machine pressure measurement and a calibrated model of the tubing flow resistance.

Estimator Calculations

According to an embodiment, the unknown leak compensation controller determines the average leak flow over the last breath and calculates the leak compensation factor, $K_L$ to minimize this flow on subsequent breaths. This control is updated at the start of every breath according to the rising transition of the IE signal.

$$K_L(k) = \min\{\max\{K_{Lsum}(k), K_{Lmin}\}, K_{Lmax}\} \quad (23)$$

$$K_{Lsum}(k) = Q_{leakIntIn}(k) K_L(k-1) \quad (24)$$

$$Q_{leakIntIn}(k) = \beta \hat{Q}_{leakTotal}(k) \quad (25)$$

where, according to an embodiment, $K_{Lmax} = 10.0$; $K_{Lmin} = 0.0$; $\beta = 2.0$; and $K_L(0) = 1$. These values of leak factor allow between zero and ten times the value of the total known leak (mask and exhalation port):

$$I_{inhIN}(n) = \frac{\hat{Q}_{LNIV}(n)}{60} \quad (26)$$

$$I_{inhOUT}(n) = \begin{cases} 0.001 & \text{if } (StartOfInh(n-1) == 1) \text{ OR } (Q_{Lreset} == 1) \\ \Delta T \cdot I_{inhIN}(n) + I_{inhOUT}(n-1) & \text{otherwise} \end{cases} \quad (27)$$

$$\hat{Q}_{leakTotal}(k) = \begin{cases} \dfrac{I_{inhOUT}(n)}{BreathPeriod(k-1)} & \text{if } (StartOfInh(n) == 1) \\ \hat{Q}_{leakTotal}(k-1) & \text{otherwise} \end{cases} \quad (28)$$

where, according to an embodiment, $\hat{Q}_{leakTotal}(0)=0$ and $I_{inhOUT}(0)=0.001$. For NIV, $Q_{Lung\_dry}(n)=Q_L(n)$, $Q_{Lung\_dry}(n)$ shall be converted to the BTPS reference frame according to the conversion formula.

Experimental Results

Figure 7:
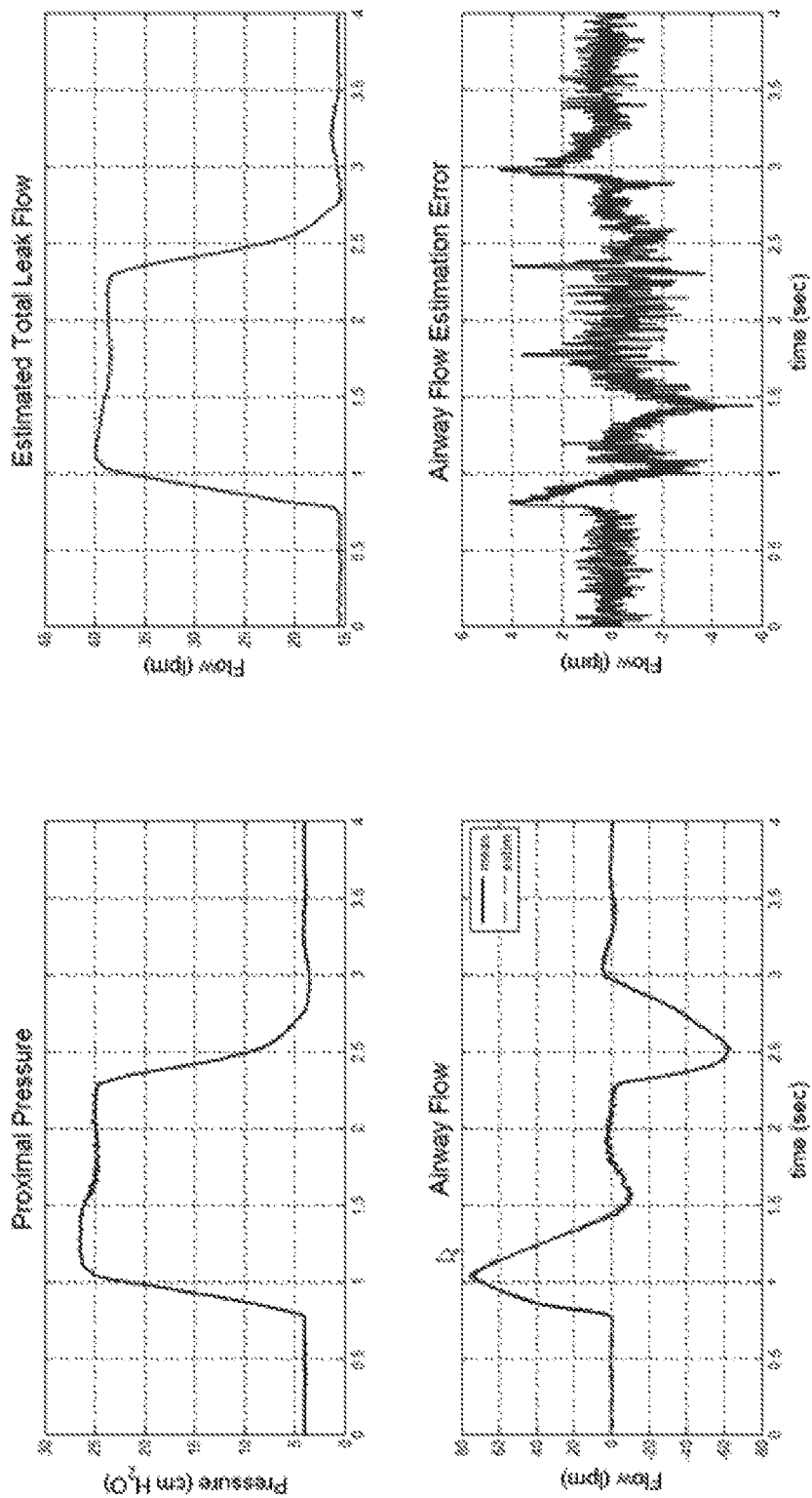
FIG. 7 is a series of graphs for proximal pressure, estimated total leak flow, airway flow, and airway flow estimation error, in accordance with an embodiment.
Figure 8:
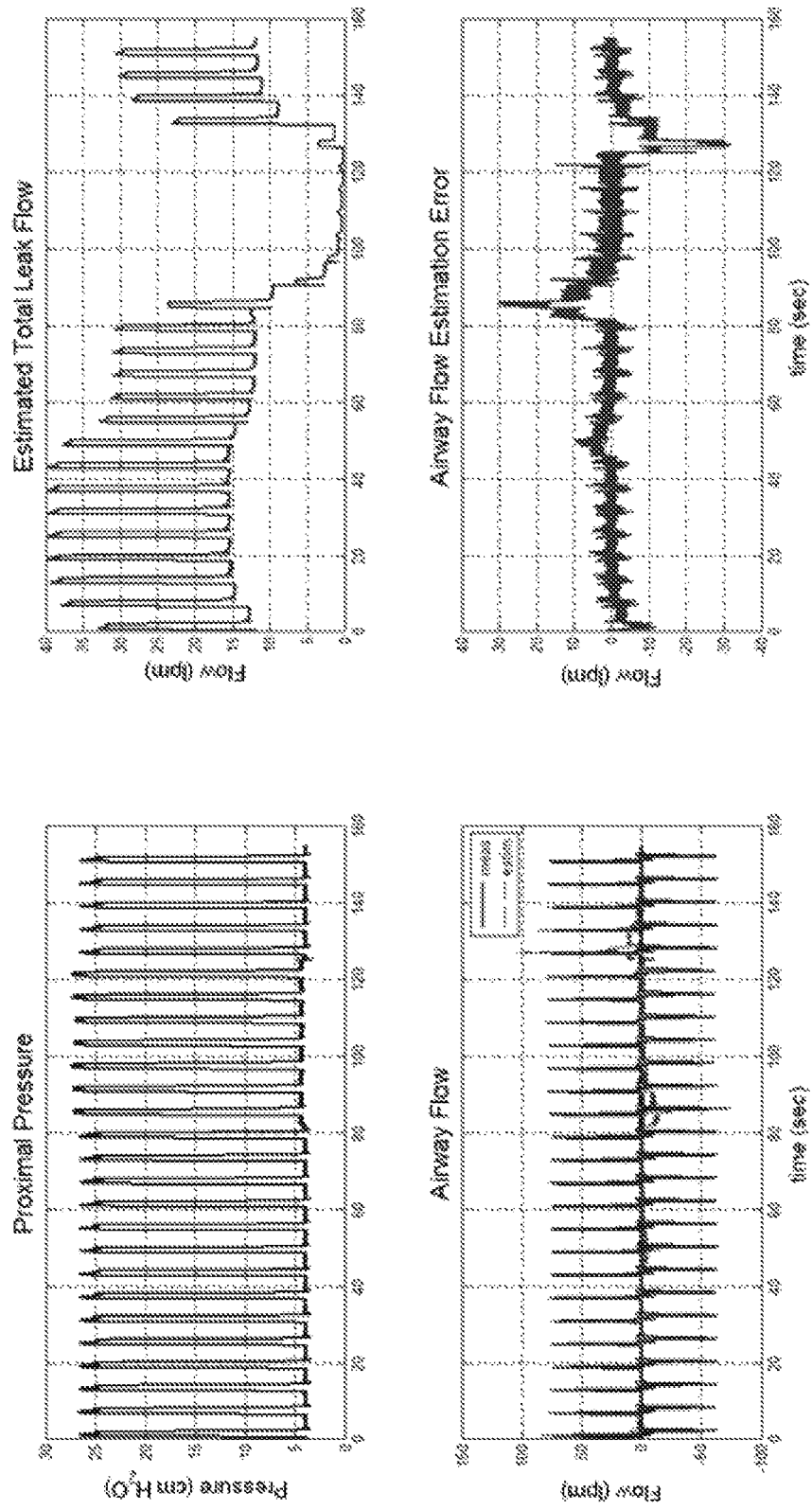
FIG. 8 is a series of graphs for proximal pressure, estimated total leak flow, airway flow, and airway flow estimation error, in accordance with an embodiment.

According to one embodiment, the estimator method and system was built using Simulink software and subsequently specified for software implementation in an NIV product. An example single breath pressure and flow waveforms ventilating a Michigan Instruments Training and Test Lung are shown in FIG. 7. Lung compliance was set to about 0.02 liters/cm $H_2O$ and an Rp5 airway restriction was used. A Respironics 22 mm BiPAP circuit with DEP exhalation port leak was used. Circuit compliance was calibrated at 0.0008 liters/cm $H_2O$ and the known leak as 97 cm $H_2O/(1/sec)^2$. A measured lung flow error of about 1.5 lpm rms was achieved with peak errors on breath transition of less than 6 lpm. FIG. 8 illustrates a series of breaths. A sudden unknown leak step change is introduced in the circuit connection after the first breath (~5 sec). The leak is then removed at 50 seconds. At 85 seconds the known leak is almost fully occluded. From these series of disturbing actions the total leak estimate responds and the airway flow estimate (dashed line) rapidly recovers within a few breaths.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The invention claimed is:

1. A method for estimating patient airway flow in a non-invasive ventilator system, the method comprising the steps of:
   providing a non-invasive ventilator system, the non-invasive ventilator system comprising tubing having a distal ventilator end and a proximal patient end;
   obtaining a measurement of tubing compliance and a measurement of one or more parameters of a nonlinear leak flow model of the non-invasive ventilator system comprising leak flow resistance;
   measuring, using a distal gas flow sensor of the non-invasive ventilator system, gas flow at the distal ventilator end of the tubing;
   measuring, using a proximal pressure sensor of the non-invasive ventilator system, pressure at the proximal patient end of the tubing;
   determining an estimated gas flow at the proximal patient end of the tubing, the estimated gas flow comprising the measurement of gas flow at the distal ventilator end of the tubing, the measurement of pressure at the proximal patient end of the tubing, the obtained measurement of tubing compliance, and the obtained measurement of the one or more parameters of the nonlinear the leak flow model comprising leak flow resistance;
   determining a proximal pressure error value by subtracting the measured pressure at the proximal patient end of the tubing from an estimated pressure at the proximal patient end of the tubing;
   compensating, using a compensator, for the determined proximal pressure estimate error value;
   compensating for at least one error in the estimated gas flow at the proximal patient end of the tubing by feeding the estimated gas flow back into a sum of accumulated flows;
   determining an estimated gas flow leak, the estimated gas flow leak comprising the estimated pressure at the proximal patient end of the tubing and the obtained measurement of the one or more parameters of the nonlinear leak flow model comprising the leak flow resistance;
   monitoring for an unknown leak in the non-invasive ventilator system using a feedback controller to estimate a size of the unknown leak during ventilation;
   determining, when the unknown leak is identified, a gas flow leak correcting factor comprising leak information from a previous breath;
   adjusting, with the determined gas flow leak correcting factor, the estimated gas flow leak; and
   compensating for bias in the patient airway flow.

2. The method of claim 1, wherein the step of obtaining the measurement of the one or more parameters of the nonlinear leak flow model comprising the leak flow resistance comprises determining one or more calibration measurements during a calibration procedure prior to breath delivery.

3. The method of claim 1, further comprising the step of comparing the gas flow leak correcting factor to a predetermined lower limit.

4. The method of claim 3, wherein an alarm is triggered if the gas flow leak correcting factor is below the predetermined lower limit.

5. The method of claim 1, further comprising the step of comparing the gas flow leak correcting factor to a predetermined upper limit.

6. The method of claim 5, wherein an alarm is triggered if the gas flow leak correcting factor is above the predetermined upper limit.

7. The method of claim 1, wherein the compensator is a proportional-integral compensator that utilizes the following equation:

$$\hat{Q}_L = \left(\frac{K_i + K_p s}{s}\right)(P_p - \hat{P}_p).$$

8. The method of claim 1, further comprising the step of suspending estimation when the gas flow at the distal ventilator end of the tubing or the pressure at the proximal patient end of the tubing cannot be measured, wherein the step of suspending estimation comprises suspending the estimated gas flow or the estimated gas leak flow.

9. A non-invasive ventilator system, comprising:
   airway tubing comprising a distal ventilator end and a proximal patient end;
   a distal gas flow sensor configured to measure gas flow at the distal ventilator end of the airway tubing, the distal gas flow sensor comprising a blower flow sensor;
   a proximal pressure sensor configured to measure pressure at the proximal patient end of the airway tubing; and
   a gas flow controller configured to supply a determined volume of gas to the distal ventilator end of the airway tubing, wherein the gas flow controller is configured to determine the supplied volume of gas by: (i) determining an estimated gas flow at the proximal patient end of the airway tubing, the estimated gas flow comprising a measurement of gas flow at the distal ventilator end of the airway tubing, a measurement of pressure at the proximal patient end of the airway tubing, a measurement of tubing compliance, and a measurement of one or more parameters of a nonlinear leak flow model comprising leak flow resistance; (ii) determining a proximal pressure error value by subtracting a measured pressure at the proximal patient end of the airway tubing from an estimated pressure at the proximal patient end of the airway tubing; (iii) compensating for the determined proximal pressure estimate error value; (iv) compensating for at least one error in the estimated gas flow at the proximal patient end of the airway tubing by feeding the estimated gas flow back into a sum of accumulated flows; (v) determining an estimated gas flow leak, the estimated gas flow leak comprising the estimated pressure at the proximal patient end of the airway tubing and the obtained measurement of one or more parameters of the nonlinear leak flow model comprising the leak flow resistance; (vi) monitoring for an unknown leak in the non-invasive ventilator system using a feedback controller to estimate a size of the unknown leak during ventilation; (vii) determining, when the unknown leak is identified, a gas flow leak correcting factor comprising leak information from a previous breath; (viii) adjusting, with the determined gas flow leak correcting factor, the estimated gas flow leak; and (ix) compensating for bias in the patient airway flow.

10. The non-invasive ventilator system of claim 9, wherein the controller comprises a compensator configured to compensate for the determined proximal pressure estimate error value.

11. The non-invasive ventilator system of claim 10, wherein the compensator is a proportional-integral compensator that utilizes the following equation:

$$\hat{Q}_L = \left(\frac{K_i + K_p s}{s}\right)(P_p - \hat{P}_p).$$

12. The non-invasive ventilator system of claim 9, wherein the controller is further configured to obtain the measurement of tubing compliance and the measurement of one or more parameters of the nonlinear leak flow model during a calibration procedure or from a database.

13. The non-invasive ventilator system of claim 9, wherein the controller is further configured to compare the gas flow leak correcting factor to a predetermined lower limit.

14. The non-invasive ventilator system of claim 13, wherein the controller is further configured to trigger an alarm if the gas flow leak correcting factor is below the predetermined lower limit.

15. The non-invasive ventilator system of claim 9, wherein the controller is further configured to compare the gas flow leak correcting factor to a predetermined upper limit.

16. The non-invasive ventilator system of claim 15, wherein the controller is further configured to trigger an alarm if the gas flow leak correcting factor is above the predetermined upper limit.

17. The non-invasive ventilator system of claim 9, wherein the controller is further configured to suspend at least one of the estimations comprising the estimated gas flow and the estimated gas leak flow when the gas flow at the distal ventilator end of the tubing or the pressure at the proximal patient end of the tubing cannot be measured.

18. The non-invasive ventilator system of claim 17, wherein the controller is further configured to suspend at least one of the estimations comprising the estimated gas flow and the estimated gas leak flow when the controller determines that circuit model behavior has been compromised by one of a standby, circuit disconnect, or emergency ventilation condition.

19. The non-invasive ventilator system of claim 17, wherein when the pressure at the proximal patient end of the tubing cannot be measured, an alternate proximal pressure estimate is substituted for the measurement based on an inlet circuit flow, a machine pressure measurement, and a calibrated model of tubing flow resistance.

* * * * *